(12) United States Patent
Slade et al.

(10) Patent No.: US 9,957,464 B2
(45) Date of Patent: May 1, 2018

(54) METHODS AND DEVICES FOR PRODUCING BIODIESEL AND PRODUCTS OBTAINED THEREFROM

(71) Applicant: Renewable Energy Group, Inc., Ames, IA (US)

(72) Inventors: David A Slade, Ames, IA (US); Cody J Ellens, Ankeny, IA (US); Bradley N Albin, Ames, IA (US); Derek J Winkel, Ankeny, IA (US); Jared A Downey, Ames, IA (US)

(73) Assignee: Renewable Energy Group, Inc., Ames, IA (US)

( * ) Notice: Subject to any disclaimer, the term of this patent is extended or adjusted under 35 U.S.C. 154(b) by 0 days. days.

(21) Appl. No.: 14/897,174

(22) PCT Filed: Jun. 10, 2014

(86) PCT No.: PCT/US2014/041708
§ 371 (c)(1),
(2) Date: Dec. 9, 2015

(87) PCT Pub. No.: WO2014/201001
PCT Pub. Date: Dec. 18, 2014

(65) Prior Publication Data
US 2016/0145536 A1     May 26, 2016

Related U.S. Application Data (60) Provisional application No. 61/833,504, filed on Jun. 11, 2013.

(51) Int. Cl.
*C11B 13/00* (2006.01)
*C12P 7/64* (2006.01)
(Continued)

(52) U.S. Cl.
CPC ............. *C11B 13/00* (2013.01); *C10L 1/026* (2013.01); *C11C 1/10* (2013.01); *C11C 3/003* (2013.01);
(Continued)

(58) Field of Classification Search
USPC ......................................................... 554/174
See application file for complete search history.

(56) References Cited

U.S. PATENT DOCUMENTS

| 1,659,790 A | 2/1928 | Starrels |
| 2,290,609 A | 7/1942 | Goss et al. |

(Continued)

FOREIGN PATENT DOCUMENTS

| DE | 19724018 | 12/1998 |
| EP | 0591019 | 4/1994 |

(Continued)

OTHER PUBLICATIONS

Mosali, The Fina! Treatment. Blodlesel Magaiine •The Latest News and Data About Biodlesel Production, May 2012 May 2012), p. 1-2.*

(Continued)

*Primary Examiner* — Deborah D Carr
(74) *Attorney, Agent, or Firm* — Nyemaster Goode, PC (57) ABSTRACT

Methods and devices for economically producing a purified biodiesel product from feedstocks. Some embodiments of the methods comprise using at least one of a crude feedstock pretreatment process and a free fatty acid refining process prior to transesterification and the formation of crude biodiesel and glycerin. The crude biodiesel is then subjected to at least one biodiesel refining process which, in conjunction with feedstock pretreatment and free fatty acid refining produces a purified biodiesel product that meets multiple commercial specifications. A wide variety of feedstocks may (Continued)

be used to make biodiesel that otherwise would not meet the same commercial specifications, including corn oil, used cooking oil, poultry fats, fatty acid distillates, pennycress oil, and algal oils. The combination of feedstock refining and biodiesel refining processes is necessary to reduce problems associated with feedstocks having waxes, high free fatty acid levels, unacceptable color, high unsaponifiables levels, and high sulfur levels.

30 Claims, 2 Drawing Sheets

(51) Int. Cl.
C10L 1/02 (2006.01)
C11C 1/10 (2006.01)
C11C 3/00 (2006.01)

(52) U.S. Cl.
CPC ....... *C12P 7/649* (2013.01); *C10L 2200/0476* (2013.01); *C10L 2270/026* (2013.01); *C10L 2290/543* (2013.01); *Y02E 50/13* (2013.01); *Y02W 30/74* (2015.05)

(56) References Cited

U.S. PATENT DOCUMENTS

| | | |
|---|---|---|
| 2,383,580 A | 8/1945 | Arrowsmith et al. |
| 2,383,581 A | 8/1945 | Ross et al. |
| 2,383,596 A | 8/1945 | Dreger |
| 2,383,601 A | 8/1945 | Keim |
| 2,383,632 A | 8/1945 | Trent |
| 2,385,599 A | 9/1945 | Ball et al. |
| 2,494,366 A | 1/1950 | Sprules et al. |
| 2,543,421 A | 2/1951 | Price et al. |
| 2,588,435 A | 3/1952 | Van Loon et al. |
| 2,808,421 A | 10/1957 | Brokaw |
| 2,875,221 A | 2/1959 | Birnbaum |
| 3,102,129 A | 8/1963 | Birnbaum et al. |
| 3,459,736 A | 8/1969 | Dalibor |
| 4,164,506 A | 8/1979 | Kawahara |
| 4,267,393 A | 5/1981 | Torck et al. |
| 4,303,590 A | 12/1981 | Tanaka et al. |
| 4,364,743 A | 12/1982 | Erner |
| 4,371,470 A | 2/1983 | Matsukura et al. |
| 4,668,439 A | 5/1987 | Billenstein et al. |
| 4,695,411 A | 9/1987 | Stern et al. |
| 4,698,186 A | 10/1987 | Jeromin et al. |
| 4,839,287 A | 6/1989 | Holmberg et al. |
| 4,956,286 A | 9/1990 | Macrae |
| 5,354,878 A | 10/1994 | Connemann et al. |
| 5,399,731 A | 3/1995 | Wimmer |
| 5,424,467 A | 6/1995 | Bam et al. |
| 5,434,279 A | 7/1995 | Wimmer |
| 5,514,820 A | 5/1996 | Assmann et al. |
| 5,525,126 A | 6/1996 | Basu et al. |
| 5,578,090 A | 11/1996 | Bradin |
| 5,646,311 A | 7/1997 | Hunt et al. |
| 5,697,986 A | 12/1997 | Haas |
| 5,713,965 A | 2/1998 | Foglia et al. |
| 5,847,239 A | 12/1998 | Davey et al. |
| 5,908,946 A | 6/1999 | Stern et al. |
| 5,972,057 A | 10/1999 | Hayafuji et al. |
| 6,013,817 A | 1/2000 | Stern et al. |
| 6,015,440 A | 1/2000 | Noureddini |
| 6,090,959 A | 7/2000 | Hirano et al. |
| 6,127,560 A | 10/2000 | Stidham et al. |
| 6,127,561 A | 10/2000 | Jeromin et al. |
| 6,174,501 B1 | 1/2001 | Noureddini |
| 6,211,390 B1 | 4/2001 | Peter et al. |
| 6,262,285 B1 | 7/2001 | McDonald |
| 6,288,251 B1 | 9/2001 | Tsuto et al. |
| 6,398,707 B1 | 6/2002 | Wu et al. |
| 6,399,800 B1 | 6/2002 | Haas et al. |
| 6,440,057 B1 | 8/2002 | Ergun et al. |
| 6,489,496 B2 | 12/2002 | Barnhorst et al. |
| 6,500,974 B2 | 12/2002 | Thengumpillil et al. |
| 6,642,399 B2 | 11/2003 | Boocock |
| 6,696,283 B1 | 2/2004 | Brierley et al. |
| 6,705,158 B1 | 3/2004 | Louden |
| 6,822,105 B1 | 11/2004 | Luxem et al. |
| 6,965,043 B1 | 11/2005 | Kenneally et al. |
| 7,087,771 B2 | 8/2006 | Luxem et al. |
| 7,528,272 B2 | 5/2009 | Alasti |
| 2002/0111504 A1 | 8/2002 | Peter et al. |
| 2002/0156305 A1 | 10/2002 | Turck |
| 2003/0032826 A1 | 2/2003 | Hanna |
| 2003/0083514 A1 | 5/2003 | Boocock |
| 2003/0149289 A1 | 8/2003 | Suppes |
| 2003/0229238 A1 | 12/2003 | Fleisher et al. |
| 2004/0158096 A1 | 8/2004 | Nestler et al. |
| 2006/0074256 A1 | 4/2006 | Alasti |
| 2007/0167642 A1 | 7/2007 | Oku et al. |
| 2007/0277429 A1 | 12/2007 | Jackam et al. |
| 2008/0282606 A1* | 11/2008 | Plaza ...................... C10L 1/026 44/308 |
| 2012/0240452 A1* | 9/2012 | Erdoes, Jr. ............... B01J 8/006 44/388 |
| 2012/0266527 A1* | 10/2012 | Erdoes, Jr. ................ C10L 1/19 44/388 |

FOREIGN PATENT DOCUMENTS

| | | |
|---|---|---|
| EP | 0708813 | 2/2001 |
| EP | 1894913 | 3/2008 |
| GB | 587532 | 4/1947 |
| GB | 612667 | 11/1948 |
| GB | 2350618 | 12/2000 |
| JP | 09-327018 | 9/1998 |
| JP | 2005-015562 | 1/2005 |
| JP | 2005-060587 | 3/2005 |
| WO | 95/02661 | 1/1995 |
| WO | 9924387 | 5/1999 |
| WO | 02/28811 | 4/2002 |
| WO | 02/38529 | 5/2002 |
| WO | 2008007231 | 1/2008 |
| WO | 2012140111 | 10/2012 |
| WO | PCT/US14/41708 | 6/2014 |

OTHER PUBLICATIONS

International Search Report and the Written Opinion of the International Searching Authority, dated Oct. 1, 2014.
Mosali, "The Final Treatment." Biodiesel Magazine—The Latest News and Data About Biodiesel Production, May 1, 2012, p. 1-2, [online] downloaded from the internet. http://www.biodieselmagazine.com/articles/8477/the-final-treatment.
Third Party Observation filed in Applicant's corresponding parent European Patent Application 07735841.4, Jul. 24, 2012.
Muniyappa et al; Improved Conversion of Plant Oils and Animal Fats into Biodiesel and Co-Product; Jun. 1996; Elsevier Science Limited, 0960-8524/96 (Abstract).
Tyson, Biodiesel Research Progress 1992-1997; pp. 1-301; National Renewable Energy Laboratory; Boulder CO, Feb. 1997.
Gerpen et al; Biodiesel Production Technology Aug. 2002-Jan. 2004; pp. 1-106; Jul. 2004 National Renewable Energy Laboratory; Boulder, CO.
Biodiesel in North America: Implementation Issues; IEA Bioenergy Task 39; pp. 1-165; Feb. 28, 2004; S&T Consultants Inc, Canada.
Hildebrandt; Kinetic Investigation of the Base-Catalyzed Glycerolysis of Fatty Acid Methyl Esters; pp. 1-183; Nov. 5, 2004.
Lago, R.C.A., R.R. Szpiz, F.H. Jablonka, D.A. Pereira and L. Hartman; "Extraction and Transesterification of Vegetable Oils with Ethanol". pp. 147-154; vol. 40, No. 3; Oleagimeux; Paris, France, 1985.
MA, Fangrui and Milford A. Hannah; "Biodiesel Production: a review"; pp. 1-15; vol. 70, No. 1; Biosource Technology Elseiver, GB, 1999.

(56) References Cited

OTHER PUBLICATIONS

Kiss, A.A., A.C. Dimian, F. Omota, "Sustainable biodiesel production by integrated process design", 2005 van't Hoff Institute for Molecular Sciences, University of Amsterdam, The Netherlands, 2005.
Noureddini et al., Glycerolysis of Fats and Methyl Esters, JAOCS, 1997, pp. 419-425, vol. 74, No. 4, Lincoln NE.
Tyson, Brown Grease Feedstocks for Biodiesel, WWW domain nrel.gov, 2002, pp. 1-33, Nation Renewable Energy Technology, CO.
Tyson, Biodiesel Technology and Feedstocks, WWW domain nrel.gov, 2002, pp. 1-37, Nation Renewable Energy Technology, CO.
Clements, Pretreatment of High Free Fatty Acid Feedstocks, Biodiesel Production Technology Workshop III, Mar. 26, 2003, pp. 78c-78i; Iowa State University, Lincoln NE.
Yuan, W. et al. Vapor pressure and normal boiling point predictions for pure methyl esters and biodiesel fuels. Fuel 84, 2005, 943-950.
Gouw, T.H. et al. Physical Properties of Fatty Acid Methyl Esters. I. Density and Molar Volume. The Journal of the American Oil Chemists' Society, 41, 1964, 142-145.

\* cited by examiner

METHODS AND DEVICES FOR PRODUCING BIODIESEL AND PRODUCTS OBTAINED THEREFROM

FIELD OF THE INVENTION

The present invention generally relates to processing low-cost feedstocks into high quality biodiesel that meets multiple commercial biodiesel specifications.

BACKGROUND

Biodiesel is a renewable, clean-burning petroleum diesel replacement that enhances independence from imported petroleum, reduces greenhouse gas emissions, supports agriculture and rural economies, and creates jobs.

While biodiesel provides many benefits, biodiesel production must be economical in order to maintain supply of the advanced biofuel. Producers must adapt to changing market conditions with new processes for converting low-cost feedstocks while meeting stringent product quality specifications.

Biodiesel finished product quality standards have evolved over recent years. Currently, to ensure product consistency and protect the consumer, biodiesel quality is regulated according to various commercial standards, including ASTM D6751, EN 14214, CAN/CGSB 3.524, and numerous customer-specific specifications. The aforementioned specifications require biodiesel to be produced with tight tolerances for many properties, including flash point, residual alcohol, water and sediment, kinematic viscosity, sulfated ash, oxidation stability, sulfur, copper strip corrosion, cetane number, cloud point, carbon residue, Acid Number, cold soak filterability, monoglycerides, total and free glycerin, phosphorous, 90% distillation temperature, calcium and magnesium, sodium and potassium, particulate contamination, and ester content. The most recent revision of ASTM D6751, D6751-12, introduced multiple biodiesel grades with different limits for Cold Soak Filtration test time and monoglyceride content, further increasing the importance of these two properties for customer acceptance of biodiesel.

As specifications for biodiesel become more rigorous than anticipated by earlier designers of production processes and as demand for lower cost and non-food feedstocks increases, biodiesel producers have an urgent need to improve their production processes to allow the use of new and/or low-cost feedstocks in order to compete and remain economically viable. However, low cost feedstocks contain a variety of low level impurities that can negatively impact biodiesel quality according to the aforementioned commercial specifications.

Corn oil is an example of a promising lower cost, non-food biodiesel feedstock that contains impurities that prevent traditional biodiesel plants from using it to produce biodiesel that meets all commercial specifications. In 2005, the U.S. produced 42 percent of the world's corn. As of September 2012, the United States had the nameplate capacity to produce approximately 14 billion gallons of ethanol in 211 operational ethanol plants. As of only a few years ago, market conditions changed allowing it to be profitable for ethanol producers to separate corn oil from the byproducts of ethanol production. To demonstrate the potential volume of corn oil that could be recovered from ethanol plants, a 100 MGPY ethanol plant is theoretically able to produce 7 million gallons of corn oil annually.

Much of the corn oil that has been recovered to date has been sold for use in animal feeds and for industrial uses since it poses a number of challenges for biodiesel production. Corn oil contains wax compounds that cause biodiesel to fail the Cold Soak Filtration test in ASTM D6751 when processed in traditional biodiesel production processes. It has proven difficult to remove these waxes from the finished biodiesel product, in part because of their solubility in biodiesel alkyl esters across a wide temperature range. Waxes can be partially removed using cold filtration technology or other winterization techniques. An embodiment of the invention disclosed herein successfully removes a vast majority of these waxes so as to efficiently meet ASTM D6751 specification requirements.

Corn oil from ethanol plants also contains elevated free fatty acid (FFA) content. The FFA content of this corn oil may be between about 4 and 15 wt %. In general, high FFA feedstocks are difficult to process into biodiesel by base-catalyzed transesterification because the FFAs are converted to soaps leading to undesirable processing consequences (e.g., emulsion formation and increased catalyst costs), yield losses, and production rate downturns. The invention disclosed herein allows nearly any feedstock to be processed, regardless of its initial FFA content. As described below in detail, the invention includes multiple embodiments for reducing FFA in the feedstocks (i.e., deacidifying them) prior to transesterification, including conversion to soaps followed by physical removal, physical removal by distillation, and/or chemical conversion by esterification with an alcohol, such as methanol, ethanol, or glycerol.

In some cases even after feedstock pretreatment with an FFA reduction process, residual FFA levels can still remain higher than desirable for traditional biodiesel production, which can result in higher Acid Number values in the finished biodiesel. This is of particular concern for biodiesel produced from feedstocks such as corn oil and some fatty acid distillates. When corn oil, corn oil biodiesel, and fatty acid distillates (along with biodiesel produced therefrom) are analyzed for Acid Number with ASTM D664 Method B, they reveal a second inflection point in the titration curve caused by compounds that are neutralized after the free fatty acids. This additional inflection point causes the feedstock to exhibit an Acid Number greater than would be predicted by its true FFA content, and this Acid Number increase can be imparted to the resulting biodiesel. One of the embodiments of the invention disclosed herein efficiently reduces the quantities of both FFAs and the compounds that cause the second inflection point such that the finished biodiesel more easily and more predictably meets commercial biodiesel specifications for Acid Number.

In addition to having higher FFA levels than conventional commodity fats and oils, lower cost, non-food feedstocks for biodiesel are often much darker in color and higher in sulfur content. In traditional production processes, the darker color and a significant portion of the sulfur content are largely imparted to the finished biodiesel, which can create barriers to meeting commercial specifications and to customer acceptance in general. For example, corn oil sourced from ethanol processes customarily retains a deep red color. The red color of the resulting biodiesel gives the appearance of fuel that has been dyed, which is the established governmental regulatory method to clearly advise wholesalers, retailers and consumers that a diesel product is for off-road use only. Red-dyed diesel fuel has critical tax implications and is therefore strictly regulated. In commercial distribution of biodiesel made from ethanol-sourced corn oil, fuel retailers and end-users have expressed deep concern about using this fuel for on-road applications, even to the point of refusing to accept the product. It is important to overcome this failure of market acceptance. Our research indicates that this red coloration can be reduced to acceptable orange, yellow, or even clear colorations depending on the embodiment of this invention that is chosen for processing the feedstock and purifying the biodiesel. For example, some biodiesel filter aids may reduce the intensity of the red color, but only to a limited extent. It is costly and inefficient to sufficiently eliminate the red color by use of biodiesel filter aids alone. However, removing free fatty acids from the corn oil by distillation and then purifying the eventual biodiesel with filter aids will produce biodiesel with a commercially acceptable color.

Similarly, certain filter aids can reduce the sulfur content of biodiesel made from lower cost, non-food feedstocks with high sulfur levels, but again this process is cost prohibitive to produce biodiesel that is competitively priced with petroleum diesel. An embodiment of the present invention efficiently removes the impurities that cause unacceptable colors and/or high sulfur content of the finished biodiesel product, thereby providing a fuel which will have unrestricted acceptance in the market.

In addition to higher sulfur content and coloration issues, lower cost, non-food feedstocks can also contain significant quantities of high molecular weight, low volatility unsaponifiable components which are soluble in both the oil and the resulting biodiesel and therefore cannot be easily removed in conventional biodiesel processes. The presence of these impurities may lower the perceived quality of the finished biodiesel product and/or impact its performance in certain operating conditions. Further, such impurities reduce the ester content of the finished biodiesel and thereby create potential specification issues under EN 14214, CAN/CGSB 3.524, and numerous customer-specific specifications in the United States. Corn oil in particular contains markedly high levels of unsaponifiable components. An embodiment of the invention disclosed efficiently removes these unsaponifiable impurities to produce a higher quality biodiesel with improved market acceptance.

Although the supply of corn oil is expected to increase significantly in the near future, the characteristics described above pose significant challenges for biodiesel producers who wish to make and market biodiesel made from it. Similar biodiesel quality and customer acceptance obstacles also impede the current and future use of other emerging low cost, non-food feedstocks for biodiesel production, including used cooking oils, poultry fats, brown grease, fatty acid distillates, pennycress oil, and algal oils.

In sum, the biodiesel industry has historically used a majority proportion of higher purity feedstocks (often edible oils and fats) and has been restricted by fewer and less stringent product acceptance specifications. As the industry and its customers have evolved, pricing and availability of higher purity feedstocks have pushed the industry to explore the use of lower cost, less pure feedstocks while it simultaneously faces tightening acceptance specifications and commercial requirements for the finished product. Further, these lower cost feedstocks are not consistent in the nature and content of their impurities and exhibit great variation based not only on the underlying source of the oil, but on its production process and other variables associated with the recovery of the oils from their source materials. Conventional oil degumming pretreatment processes alone will no longer allow production of biodiesel that is universally commercially acceptable. As a result, what has been absent in the biodiesel production processes are methods, systems, and compositions that allow biodiesel producers to economically convert lower cost, non-food feedstocks such as corn oil, used cooking oil, poultry fats, brown grease, fatty acid distillates, pennycress oil, and algal oils into high-quality biodiesel that can and will conform to the various commercial biodiesel specifications in their current and future forms. More specifically, it is necessary to be able to produce biodiesel from such feedstocks via methods and systems that overcome potential specification problems associated with feedstocks that contain any combination of a variety of problem properties such as waxes, unsaponifiables, varying FFA levels, unacceptable color, and high sulfur levels.

BRIEF DESCRIPTION OF THE DRAWINGS

The advantages of the technology described may be better understood by referring to the descriptions below with the accompanying drawings. The drawings are not to scale and represent exemplary configurations that depict general principles of the technology which are not meant to limit the scope of the invention. Dotted lines within the figures are representative of different embodiments which may be included as part of the process.

DETAILED DESCRIPTION

The apparatus, devices, systems, products, and methods of the present invention will now be described in detail by reference to various non-limiting embodiments, including the figures which are exemplary only.

Unless otherwise indicated, all numbers expressing dimensions, capacities, and so forth used in the specification and claims are to be understood as being modified in all instances by the term "about."

The present invention may be practiced by implementing process steps in different orders than as specifically set forth herein. All references to a "step" may include multiple steps (or substeps) within the meaning of a step. Likewise, all references to "steps" in plural form may also be construed as a single process step or various combinations of steps.

The present invention may be practiced by implementing process units in different orders than as specifically set forth herein. All references to a "unit" may include multiple units (or subunits) within the meaning of a unit. Likewise, all references to "units" in plural form may also be construed as a single process unit or various combinations of units.

As used in this specification and the appended claims, the singular forms "a," "an," and "the" include plural referents unless the context clearly indicates otherwise.

As used in this specification and the appended claims, the term "fats and oils" refers to any material of biological origin both vegetable and animal which is a useful feedstock for making biodiesel. The feedstock may be in a crude form containing impurities and is considered a "crude feedstock" or "crude oil." On the other hand, the feedstock may be pretreated using other equipment to remove impurities. The pretreatment process may occur at a biodiesel production facility or at the source location or both producing a "pretreated feedstock" or "pretreated oil." The term "refined feedstock" refers to feedstocks having sufficiently low free fatty acid content to be used directly in transesterification. Refined feedstock may include crude alkyl esters. The term "free fatty acid" refers to aliphatic carboxylic acids having carbon chains with about 6 to about 24 carbon atoms. Free fatty acids may be found in fats and oils between 0 to 100 wt % and are susceptible to forming esters upon reacting with an alcohol under esterification conditions. The term "ester" is used to refer to organic esters, including mono-esters, di-esters, tri-esters, and more generally multi-esters. The term "biodiesel" is used to describe a fuel comprised of fatty acid alkyl esters of long chain fatty acids derived from fats and oils. The term "alcohol" is used to refer to an organic alcohol, including monohydric alcohols, dihydric alcohols, and polyhydric alcohols generally.

The term "wax" or "waxy compounds" refers to relatively large molecules with at least one long saturated carbon chain that are found in oils such as corn oil, canola oil, sunflower oil, olive oil, poultry fat, pennycress oil, and possibly algal oils. Waxy compounds have a high melting point (some are around 80° C.) and can cause the oil to become cloudy when cooled. Waxes have been grouped under the category of unsaponifiable material for the purposes of this discussion. Waxy compounds can cause biodiesel to fail certain cold soak filterability tests, even at concentrations less than 0.1 wt %. The term "gum" or "gums" refers to compounds (e.g., phospholipids) that may be present in a crude feedstock which tend to form insoluble precipitates when contacted with water and emulsions in base-catalyzed transesterification processes. When water is added to the crude feedstock under the appropriate conditions, gums can become hydrated (absorb water) and insoluble so that they can be removed by a centrifugal separator.

The term "Acid Number" refers to a common measurement of the amount of acid functional groups in the molecules in a sample. It specifically refers to the quantity of strong base (typically KOH) required to titrate the acid functional groups in a sample. Acid Number is conventionally expressed as milligrams of potassium hydroxide per gram of sample.

The term "sulfur" refers to the total quantity of sulfur in liquid fuels defined as mg/kg or parts per million (ppm). The term "unsaponifiables" refers to compounds in oils and fats that do not contain a fatty acid moiety that can be converted to an alkyl ester molecule and that therefore can reduce the ester content and/or yield of biodiesel. The term "cold soak filterability tests" refers to test methods included in commercial specifications such as ASTM D7501, CAN/CGSB 3.524 appendix A, and EN 14214 that are used to evaluate the potential cold weather performance of biodiesel and biodiesel blends.

The methods of the invention can accommodate a wide range of feedstocks. In some embodiments of the invention, nonexclusive examples of feedstock are fats and oils including coconut oil, palm oils, palm kernel oil, cottonseed oil, rapeseed oil, peanut oil, olive oil, linseed oil, babassu oil, tea oil, Chinese tallow oil, olive kernel oil, meadowfoam oil, chaulmoorgra oil, coriander oil, canola oil, soybean oil, corn oil, camelina oil, castor oil, pennycress oil, lard oil, jatropha oil, sunflower oil, algae oils, used cooking oils, bacon grease, choice white grease, yellow grease, brown grease, poultry fat, beef tallow, lard, and fish oils. Additionally, feedstocks may include purified or distilled fats and oils including fatty acid distillates, such as palm fatty acid distillate, and others. In some cases, distillation bottoms may be considered a low-grade crude feedstock, including bottoms from crude biodiesel distillation.

Corn oil is a feedstock of particular commercial significance for producing biodiesel. Corn oil is a co-product of the grain ethanol industry. Corn oil is typically recovered from ethanol manufacturing processes using a number of methods including solvent extraction, centrifugation, filter pressing, and other processes. Additional oils suitable for biodiesel production may be recovered from other grain ethanol processes including sorghum oil, wheat oil, and others, depending on the feedstock for the ethanol production process. After recovery, the crude oil may be further processed as desired. In one embodiment, crude oil recovered from a grain ethanol process is used for biodiesel production.

One embodiment of the present invention includes a method of using low-cost feedstocks to produce biodiesel that meets multiple commercial product specifications. The invention includes one or more feedstock pretreatment, FFA refining, and biodiesel refining embodiments which may be chosen depending on FFA content and other factors to overcome potential specification problems associated with feedstocks having waxes, high free fatty acid levels, unacceptable color, high unsaponifiable levels, and high sulfur levels. Certain feedstock pretreatment, FFA refining, and biodiesel refining embodiments described herein may be installed and used at a single biodiesel facility thereby giving the facility operator the option of choosing one process pathway for a particular feedstock and another process pathway for another feedstock depending on feedstock characteristics or other factors. The biodiesel production method disclosed may include all or fewer than all of the feedstock pretreatment, FFA refining, and biodiesel refining embodiments described herein. The particular embodiment(s) will dictate which feedstocks can be used to produce commercially acceptable biodiesel. One method for crude feedstock pretreatment and biodiesel refining can produce biodiesel having physical and chemical properties that conform to commercial specifications regardless of the feedstock properties.

Figure 1:
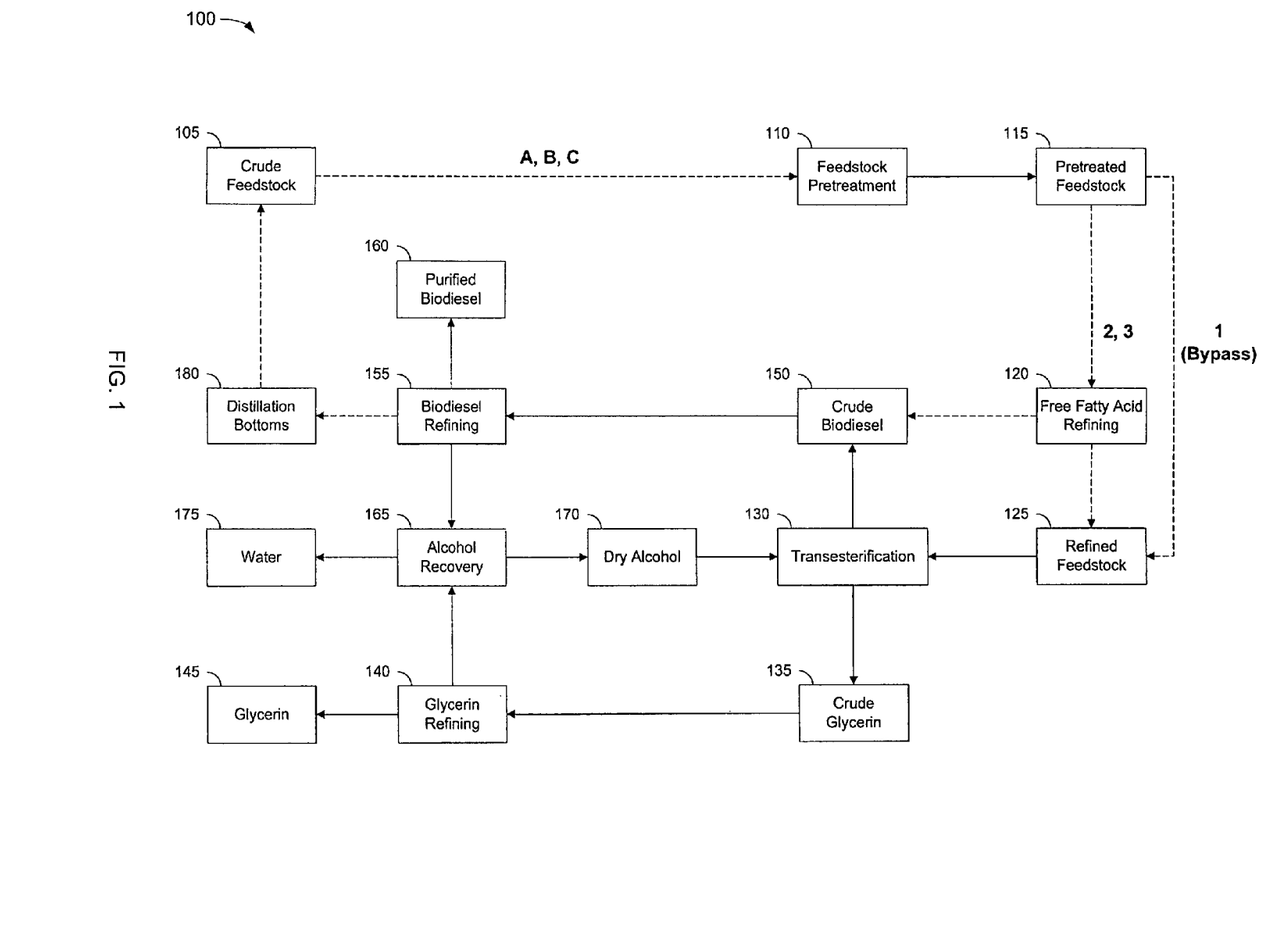
FIG. 1 is a process flow diagram showing several embodiments of methods for biodiesel production.

Crude feedstocks (105) containing various impurities require pretreatment and/or FFA refining before being subjected to a transesterification process to convert the refined feedstock to crude biodiesel (150) and finally a biodiesel purification process to make high quality purified biodiesel (160) that meets multiple commercial specifications. An exemplary method (100) with reference to FIG. 1 is outlined for processing crude feedstock (105) into glycerin (145) and purified biodiesel (160) meeting commercial product specifications. The crude feedstock (105) arrives at the biodiesel production facility and is discharged into crude feedstock storage. Compatible feedstocks may be combined and stored in a shared tank before being processed. Crude feedstock (105) first undergoes a feedstock pretreatment process (110) that depends on its FFA content and other properties to produce a pretreated feedstock (115).

The pretreated feedstock (115) may then be subjected to an FFA refining process (120) which removes and/or converts FFA by way of: FFA stripping (dashed line 2) or esterification/glycerolysis (dashed line 3) to yield a refined feedstock (125). Optionally, FFA refining (120) may yield a stream of crude biodiesel (150) in the case of FFA stripping followed by esterification of the fatty acid distillate. As another option, FFA refining (120) may yield a stream of glycerides or refined feedstock (125) in the case of FFA stripping followed by glycerolysis of the fatty acid distillate. In one embodiment, as shown by dashed line 1, pretreated feedstock (115) having sufficiently low levels of FFA to be categorized as refined feedstock (i.e., the crude feedstock was chemically refined to remove FFA in feedstock pretreatment (110) or was refined elsewhere) bypasses the FFA refining unit (120). Refined feedstock (125) is processed in a transesterification process (130) to yield crude biodiesel (150) and crude glycerin (135). Crude glycerin (135) is refined in a glycerin refining unit (140) yielding glycerin (145) which may be recycled into the FFA refining process (120) for glycerolysis. Crude biodiesel (150) undergoes a final biodiesel refining process (155) to produce a commercially-acceptable purified biodiesel product (160). Wet alcohol from biodiesel refining (155) and glycerin refining (140) is sent to an alcohol recovery unit (165) to separate water (175) and recover dry alcohol (170). Embodiments of the unit operations of FIG. 1 are described in more detail in FIG. 2.

Figure 2:
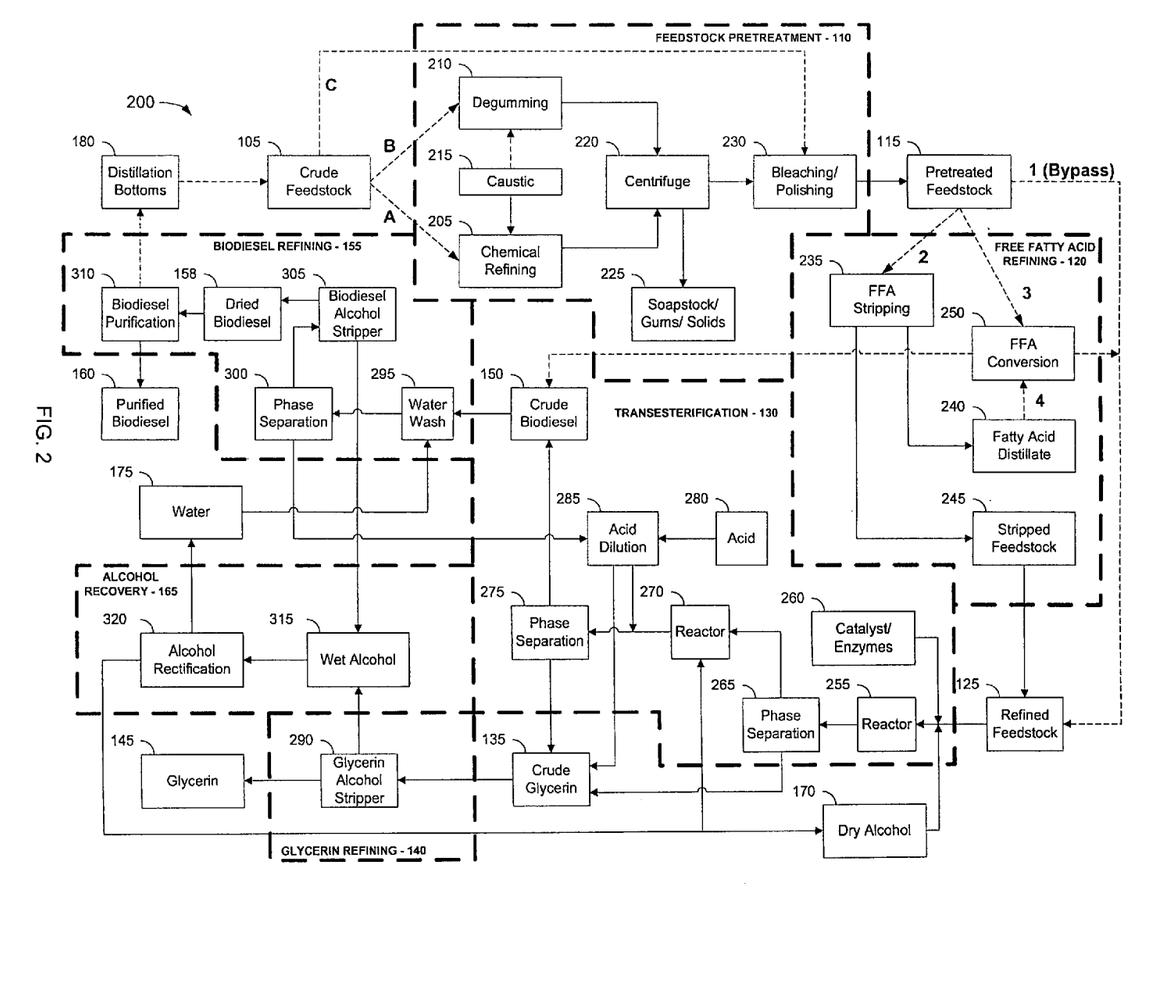
FIG. 2 is a process flow diagram showing more specific embodiments of the methods for biodiesel production shown in FIG. 1.

FIG. 2 shows process embodiments similar to the embodiments shown in FIG. 1, except FIG. 2 shows additional embodiments and process steps in more detail. Crude feedstock (105) is received into storage at the biodiesel production facility. Compatible feedstocks may be combined and stored in a shared tank before they are processed further. Crude feedstocks (105) are pretreated and refined as dictated by their FFA content and other feedstock properties. Crude feedstock (105) may undergo either a chemical refining (205) (dashed line A), degumming (210) (dashed line B), or a bleaching and polishing (230) (dashed line C) pretreatment step depending on its physical and chemical characteristics. Typically chemical refining (205) (dashed line A) is performed for crude feedstocks having a relatively low amount of FFA (<4%, for example). In one embodiment, an acid, such as phosphoric acid, may be added to the crude feedstock (105) in the chemical refining unit (205) with or without additional water. In such a process, the acid and water perform a similar function as in the degumming unit (210). Regardless of acid use, a strong base (215), such as NaOH (caustic soda) or KOH (potash), is added to the crude feedstock from unit (105) to reduce the free fatty acid content to a desired level (<0.2%, for example) by converting the FFAs to soaps and also to neutralize any added acid. In one embodiment, soapstock is composed of water, soaps, hydrated gums if present, and any other hydratable, polar, or solid components in the crude feedstock. This soapstock (225) is then removed in a centrifugal separator (220).

Alternatively, feedstocks having greater than about 4 wt % FFA are typically pretreated with a degumming step (210) (dashed line B), although in particular situations feedstocks with lower amounts of FFA may also be pretreated with degumming (210). An acid, such as phosphoric acid, may be added to the crude feedstock (105) in the degumming unit (210) which may be heated, for example, using steam (water). In such a process, the acid and water hydrate naturally-occurring gums in the oil or fat so that they can be separated from the crude feedstock. The degumming unit (210) is also capable of facilitating the removal of other hydratable and/or polar impurities in the crude feedstock as well as solids. Optionally, a base (215), such as sodium hydroxide (caustic soda), may be added to the degumming unit (210) in order to neutralize the acid used for degumming. Excess base may also be added to neutralize a minority portion of the free fatty acids.

In both embodiments described above, feedstock leaving the chemical refining unit (205) or the degumming unit (210) is processed in a centrifugal separator (220). The centrifugal separator unit (220) removes the aqueous phase and any hydratable or polar compounds from the crude feedstock formed in unit (205) or (210) in addition to any solids. This aqueous phase may be referred to as soapstock (225) in both embodiments.

Once the crude feedstock (105) has passed through the centrifugal separator (220) it may undergo one or more drying, bleaching and polishing steps in unit (230) including heat bleaching or clay bleaching steps to reduce color, solids, residual soaps, moisture and other impurities in the partially refined feedstock. With deeply colored feedstocks, the bleaching and polishing steps (230) do not typically remove enough color to eliminate the potential for commercial rejection of the resulting biodiesel. In the case where corn oil is the crude feedstock, bleaching and polishing steps (230) do not typically remove enough of the characteristic deep red color to prevent the resulting biodiesel from resembling fuel that has been dyed for off-road use only. In one embodiment the feedstock is bleached and dried in the same unit operation. In another embodiment the feedstock is dried by a vacuum-dryer, flash drum, or other such means to a desired water content either before and/or after it enters the bleaching unit. The desired water content depends on the type of filter material that is used in the bleaching unit and the impurities that are present in the feedstock at this point.

After the feedstock has been dried and bleached it enters a polishing filter where any remaining filterable impurities are removed, along with any fine particles of filter material from the bleaching step. For feedstocks containing waxy compounds, the preceding steps may remove some wax if operated at low temperatures (<150° F., for example), but since wax is somewhat soluble even at relatively low temperatures some of the waxes are retained in the feedstock and are carried through to the biodiesel. Also, the viscosity of oils and fats increases dramatically at lower temperature, which means lower refining temperatures can dramatically reduce the feasible throughput of any process unit that has to operate at a lower temperature.

In one embodiment, where corn oil, used cooking oil, fatty acid distillate, or other feedstocks are pretreated, the feedstock (105) may not necessarily require chemical refining (205), degumming (210), or centrifugation in unit (220) and may instead pass directly (dashed line C) to the bleaching and polishing unit (230) to yield a dry pretreated feedstock (115). In fact, some feedstocks may form an irresolvable emulsion in the centrifuge (220) if they are subjected to a degumming (210) and/or washing step prior to the centrifuge (220). Therefore, in one embodiment, feedstocks (105) that emulsify are not subjected to units (205) or (210) and (220) and may instead be fed directly (dashed line C) to the bleaching and polishing unit (230) after bypassing the degumming/chemical refining and centrifugal separation processes to yield a pretreated feedstock (115), Furthermore, some crude feedstocks (105) such as certain fatty acid distillates may not require feedstock pretreatment (110) at all and may therefore pass directly to FFA conversion unit (250) (dashed line 3) as a pretreated feedstock (115).

Depending on the effectiveness of the initial crude feedstock pretreatment strategy and the pretreated feedstock FFA content, the pretreated feedstock (115) may optionally undergo further processing. If free fatty acids have been removed in the chemical refining unit (205) and centrifuge (220) in the form of soapstock (225), the pretreated feedstock (115) may continue directly to the transesterification process as a refined feedstock (125) as shown by dashed line 1. However, if a significant quantity of free fatty acids remain (>0.2%, for example) because the crude feedstock (105) was pretreated with a degumming process (210) (dashed line B) and/or a bleaching and polishing step (230) (dashed line C), the pretreated feedstock (115) requires further processing in either the FFA stripping unit (235) or in the FFA conversion unit (250). Free fatty acids in the crude feedstock (105) are generally undesirable in the transesterification process (130) because they form soaps in the oil when they react with the base catalyst used to drive the transesterification reaction. Therefore, they must be either removed or converted or both. There are two primary processing options to reduce FFA levels in the pretreated feedstock (115): 1) stripping or deacidification to physically remove FFAs from the feedstock (235) and 2) chemical conversion by esterification or glycerolysis (250). Glycerolysis is a subcategory of esterification in which glycerol, an alcohol, is used to convert FFAs into glycerides, which are fatty acid esters of glycerol. An advantage of this invention over prior art is that a feedstock with any FFA content (0-100 wt %) can be processed with the appropriate feedstock pretreatment embodiment (110).

In one embodiment shown by dashed line 2, the pretreated feedstock (115) is stripped of free fatty acids along with other components of low molecular weight relative to glycerides in a physical FFA refining step using distillation (235). Although the FFA stripping step can be performed on feedstocks having any FFA level, a preferred FFA level is between about 0.2 wt % FFA and about 30 wt % FFA. The FFA stripping step (235) may employ steam, hot oil, or other thermal fluid to heat the crude feedstock. The distillation may occur under vacuum to remove free fatty acids from the oil phase by evaporation in unit (235). The FFA stripping step (235) may employ a distillation column, wiped-film evaporator, or other such equipment and it may optionally include the injection of steam into the distillation unit to facilitate the separation of the FFAs from the remainder of the feedstock. Two product streams can be produced from FFA stripping (235): a relatively pure fatty acid distillate (240) made up of greater than about 50 wt % FFA and the stripped feedstock (245) containing less than about 0.5 wt % FFA. The stripped feedstock stream (245) is sufficiently purified during FFA stripping (235) that it can enter the transesterification process as a refined feedstock (125). The fatty acid distillate stream (240) may be sold as a final product or may undergo further processing to chemically convert the FFAs in unit (250) (dashed line 4).

FFA stripping can have additional benefits beyond FFA reduction. As one example, corn oil subjected to FFA stripping in unit (235) is substantially less red than crude or esterified corn oil. That is, compounds are modified or removed along with the FFA such that biodiesel made from stripped corn oil does not resemble dyed diesel fuel.

In another embodiment, pretreated feedstock (115) is directly processed in unit (250). Feedstocks having between 0.1-100 wt % FFA can be processed in the FFA conversion unit (250) to convert FFA into esters by way of esterification or glycerides by way of glycerolysis (dashed line 3). Fatty acid distillate (240) from FFA stripping (235) may also be processed in the FFA conversion unit (250) (dashed line 4).

In one embodiment pretreated feedstock (115) (following dashed arrow 3) and/or fatty acid distillate (240) (following dashed arrow 4) is esterified to form alkyl esters in unit (250). In this embodiment free fatty acids may be esterified using a homogeneous and/or heterogeneous catalyst with an alcohol (e.g. dry alcohol from unit 170) to form fatty acid alkyl esters. The homogeneous catalyst may include sulfuric acid, methanesulfonic acid, p-toluene sulfonic acid, hydrochloric acid, or other suitable acid. The heterogeneous catalyst may include an acid ion exchange resin such as Amberlyst BD20 sulfonic acid ion exchange resin from Rohm and Haas and Lewatit® catalyst from Lanxess, other solid catalysts such as metal oxide materials, or enzymatic catalysts. Esterification of FFAs in the FFA conversion unit (250) may take place in one or more reactors and the product may be separated, washed and/or recycled back into itself until the FFA is low enough to leave as a refined feedstock (125) or blended into the refined feedstock (125). Homogeneous acid catalyst may or may not be removed and/or neutralized before leaving the FFA conversion unit (250). In one embodiment FFA in the product stream contains less than about 5 wt %, 4 wt %, 3 wt %, 2 wt %, 1 wt %, 0.5 wt %, 0.3 wt % or 0.1 wt % FFA before entering transesterification as either part or all of the refined feedstock (125). Alternatively, if fatty acid distillate (240) converted in the FFA conversion unit (250) has sufficiently high alkyl ester content or if the alkyl esters are phase separated from the product mixture the alkyl ester-rich stream may bypass transesterification (130) entirely and proceed directly to biodiesel refining (155) as crude biodiesel (150).

In the case where corn oil is the feedstock subjected to free fatty acid esterification in unit (250), the red color of the corn oil may in fact become deeper than the initial crude corn oil. Thus, the resulting corn oil biodiesel may more strongly resemble dyed petroleum diesel fuel unless it is further processed to remove the color. Similarly, the brown color of other crude feedstocks may deepen during FFA conversion in unit (250) and thus require additional processing downstream to reduce the color of the biodiesel to commercially acceptable levels. Generally speaking, discouraging color issues may be either improved or exacerbated during feedstock pretreatment (110) and FFA refining (120) but they are often exacerbated.

In another embodiment, pretreated feedstock (115) (following dashed arrow 3) and/or fatty acid distillate (240) (following dashed arrow 4) undergo glycerolysis to form glycerides in unit (250). In this embodiment, free fatty acids from the pretreated feedstock (115) or fatty acid distillate (240) may be reacted with glycerin from unit (145) in FFA conversion unit (250) to form mono-, di-, and triglycerides, which can then be transesterified to produce biodiesel. Various process equipment may be used within the FFA conversion unit (250) to accomplish this step and reduce the FFA of the products stream to less than about 5 wt %, 4 wt %, 3 wt %, 2 wt %, 1 wt %, 0.5 wt %, 0.3 wt % or 0.1 wt % FFA before entering transesterification as a refined feedstock (125).

Thus, feedstock (105) containing any quantity of FFA can be processed by at least one of the pretreatment (110) and FFA refining (120) methods described above whereby FFAs are removed in a chemical refining unit (205), a physical refining unit (235) and/or converted by esterification or glycerolysis in a FFA conversion unit (250). However, in each pretreatment (110) and FFA refining (120) approach a small amount of free fatty acids typically remains and ends up in the finished biodiesel product, which increases the biodiesel Acid Number. Because certain feedstocks can contain impurities that contribute to biodiesel Acid Number when assessed according to ASTM D664 Method B, further purification must be performed on biodiesel made from such feedstocks in order to meet commercial specifications and obtain full market acceptance. This is particularly true for biodiesel produced from feedstocks such as corn oil and some fatty acid distillates. When corn oil, corn oil biodiesel and fatty acid distillates (along with biodiesel produced therefrom) are analyzed for Acid Number with ASTM D664 Method B, they can exhibit a second titration inflection point caused by compounds that are titrated after the free fatty acids. Therefore the feedstock tends to have an Acid Number greater than the amount of FFA in the oil, and this Acid Number increase is imparted to the resulting biodiesel without additional downstream processing.

Once the feedstock has been pretreated (110) and refined (120) it enters the transesterification process (130) and then on to the biodiesel refining process (155). There are several processes that may be used to produce biodiesel from oils and fats, including base-catalyzed transesterification, acid-catalyzed transesterification and enzymatic transesterification.

In one embodiment, biodiesel is produced from feedstock using base-catalyzed transesterification in one, two, three, or more reactors. In one embodiment, refined feedstock (125) is subjected to a transesterification reaction process and then refined to produce purified biodiesel (160) and glycerin (145). This transesterification reaction is based on the chemical reaction of the mono-, di-, and triglycerides contained in the feedstock with an alcohol in the presence of a base catalyst. The base catalyst used in the transesterification reaction may be selected from several different basic materials. Suitable catalysts include, for example, NaOH or caustic soda, KOH or potash, $CH_3NaO$ (sodium methoxide), and $CH_3KO$ (potassium methoxide). The alcohol used in the transesterification reaction may be selected from, for example, methanol or ethanol.

As the transesterification reaction is carried out in a first reactor (255), dry alcohol (170) and catalyst or enzymes (260) may be delivered to the refined feedstock (125) in parallel, as separate reaction components, or the alcohol and catalyst can be delivered to the refined feedstock (125) as a mixture. When delivered as a mixture, the catalyst may be dissolved or dispersed in the alcohol by any suitable means prior to charging the mixture into the feedstock. Alternatively, the catalyst may be provided as a liquid and mixed with the alcohol, limiting the need for dissolution of the catalyst in the alcohol prior to mixing the alcohol and catalyst with the feedstock. Where the catalyst is mixed with the alcohol as a liquid, the catalyst may be added to the alcohol by, for example, one or more metering pumps. In addition, because an alkaline catalyst might be sensitive to water, the catalyst may be stored in a tank protected with a nitrogen layer. In carrying out the transesterification reaction, the dry alcohol (170), catalyst or enzymes (260), and refined feedstock (125) may be charged directly into the first reactor (255) or may be mixed before entering the reactor (255).

The reaction system can be closed to the atmosphere to prevent loss of the alcohol used in the transesterification reactor unit (255). As the reaction components are mixed, the mixture may be kept just below the boiling point of the alcohol to speed the reaction time by maximizing reaction temperature while minimizing the amount of alcohol lost during reaction. Alternatively, the reaction mixture may be heated above the boiling point of the alcohol in a vessel that is either pressurized or uses reflux to maintain the alcohol largely in a liquid state. All vessels which contain alcohol, may also be connected to a vent system to capture any alcohol vapors. Captured alcohol vapors may be fed into a condensing system that recovers the alcohol and recycles the alcohol back into the refining process. An excess amount of alcohol is typically used to ensure total conversion of the feedstock glycerides into the desired ester product.

The transesterification reaction mixture leaves the reactor (255) and enters a phase separation unit (265). In the phase separation unit (265) the reaction mixture is separated into two-phases: an ester-rich phase (crude biodiesel) that is transferred to an additional reactor or reactors (270) and a glycerin-rich phase (crude glycerin) collected in unit (135). The crude glycerin (135) is more dense than the crude biodiesel (150) and the two phases can be separated by gravity separation in a decanting vessel or, if needed or desired, by centrifugal separation.

In one embodiment, transesterification of the feedstock takes place in one or more mixing-settling process units. In such process units, the transesterification reaction occurs in a mixer or reactor and the crude biodiesel and crude glycerin resulting from the transesterification reaction form two distinct phases that can be separated by a settling process. If two or more mixing-settling process units are used, the feedstock and the intermediate product, respectively, may flow successively through the two or more mixing-settling processes. Each mixing-settling process can be supplied with the desired amount of alcohol and catalyst. The reactors included in the mixing-settling process units can be multi-stage in design, comprising various reaction chambers or zones in order to achieve maximum conversion efficiency to the ester product. The settling steps allow phase separation to approach the limit of solubility, which facilitates downstream purification of the biodiesel and glycerin products.

Once the transesterification reaction is complete in the second reactor (270), the reaction mixture enters a second phase separation unit (275). In one embodiment, acid (280) is mixed with the reaction mixture leaving reactor (270) to deactivate the transesterification catalyst before entering the phase separation unit (275). In other embodiments the catalyst is deactivated after the phase separation unit. The acid can be diluted with water (175) prior to being introduced to the reaction mixture in an acid dilution vessel (285). In the phase separation unit (275) the reaction mixture is again separated into two-phases: an ester-rich phase or crude biodiesel (150) and a glycerin-rich phase or crude glycerin (135) sent to unit (290). Each of these crude phases may include a significant amount of the excess alcohol used in the reaction. Moreover, the crude reaction products may include other impurities such as excess catalyst, soaps, salts, water, and high boiling impurities. In one embodiment, some or all of these impurities may be treated or removed from the crude reaction products before the biodiesel and the glycerin phases are separated in unit (275).

In one embodiment, after the crude biodiesel (150) and crude glycerin (135) have been separated in unit (275), crude glycerin (135) may be treated with a suitable acid from an acid dilution vessel (285) to neutralize the residual catalyst, and crude biodiesel (150) can be subjected to a water wash in unit (295) to remove glycerin, salts, and soaps. The separated crude glycerin (135) may be subjected to additional purification in an evaporation step to remove any remaining alcohol. One such distillation and drying step is performed in unit (290). The glycerin alcohol stripper (290) removes alcohol and water which is collected in a wet alcohol unit (315) leaving a glycerin product which is approximately 78-98% pure glycerin. This glycerin (145) can be further refined to a purity of about 99% or higher using additional processing techniques, such that the glycerin product is suitable for use in high purity applications such as cosmetics or pharmaceuticals.

Crude biodiesel (150) leaving the phase separation unit (275) will still include impurities and therefore must be purified in one or more unit operations. The order and number of these operations may vary depending on crude feedstock properties, pretreatment process, transesterification process, and economic feasibility. After the crude biodiesel (150) is separated from crude glycerin (135) in unit (275), it is typically subjected to further biodiesel refining (155). For example, after separation, the crude biodiesel may contain residual alcohol, glycerin, small amounts of catalyst, salts, and soaps. This may be the case even if the crude reaction products are refined to remove or neutralize impurities prior to separation. In one embodiment, crude biodiesel (150) is subjected to a flash evaporation or distillation processes to remove excess alcohol immediately after the phase separation unit (275) before the water wash unit (295). In another embodiment, crude alkyl esters (dotted arrow from the FFA conversion unit (250)) may bypass transesterification and directly enter the water wash (295) as a crude biodiesel (150) or another step in the biodiesel refining process (155). In one embodiment, crude biodiesel (150) from FFA conversion unit (250) is distilled in biodiesel refining unit (155) to produce a purified biodiesel (160) and distillation bottoms (180) which may be recycled as a crude feedstock (105) for biodiesel, used as a feedstock for other renewable fuels, or directly used as a renewable fuel product.

In one embodiment of biodiesel refining (155), crude biodiesel (150) is first washed in unit (295) in order to remove water-soluble substances such as soaps and residual catalyst. Soaps that may be present in the water wash unit (295) may be split to avoid the formation of emulsions during washing, for example, by the addition of an acid. Diluted hydrochloric acid, such as a 3.7% solution, is suitable for such an application and can be prepared and added as necessary. In one embodiment, the biodiesel wash process may simply include gentle mixing of the crude biodiesel (150) with water (175) in unit (295), which removes residual water soluble and polar impurities as they are taken up in the aqueous phase.

If the crude biodiesel (150) is processed through such a washing step in unit (295), the washed biodiesel may contain excess water. Such excess water may be removed, for example, in a phase separation unit (300). Water from the phase separation unit (300) may be recycled back to the acid dilution unit (285) for reuse. In one embodiment, the crude biodiesel (150) may be stripped of alcohol and water in the biodiesel alcohol stripper (305), which may consist of distillation vessels, distillation columns, short path distillation, wiped film evaporators, thin film evaporators, falling film evaporators, and other strategies. Water (175) is removed from wet alcohol (315) in the alcohol rectification unit (320). The water (175) can be recycled into the water wash unit (295) and the dry alcohol (170) is recycled back to the transesterification reactor(s) (255) and (270).

While some dried biodiesel (158) (output of the biodiesel alcohol stripper (305)) products made from certain edible-quality feedstocks such as canola oil, lard, and technical tallow may be ready for use, distribution, or sale after leaving the biodiesel alcohol stripper (305), dried biodiesel products made from low-cost feedstocks will not typically meet commercial biodiesel specifications even when the appropriate feedstock pretreatment (110) and FFA refining (120) options are employed. Particularly, dried biodiesel (158) made from emerging non-food feedstocks such as corn oil, used cooking oil, poultry fat, pennycress oil, fatty acid distillates, or algae oil may require additional processing after the biodiesel alcohol stripper (305) before it is ready for use, distribution, or sale. However, the combination of an appropriate biodiesel refining process (155) with an appropriate feedstock pretreatment (110) and FFA refining (120) process will provide a purified biodiesel (160) that meets commercial specifications regardless of the initial feedstock properties.

Depending on the feedstock and its impurities, the biodiesel purification unit (310) may differ. In one embodiment, the dried biodiesel (158) is subjected to a cold filtration process in unit (310) such that high melting components, such as proteins, waxes; and certain unsaponifiables, are cooled to below their solubility point and removed by filtration. In this way, the dried biodiesel (158) can be made to meet commercial cold soak filterability tests. Generally, combining the cold filtration option with feedstock pretreatment (110) and FFA refining (120) has many advantages. However, certain feedstocks may cause the filter(s) to plug more quickly and require more frequent down time for filter changes and higher operating costs. Such feedstocks include those with high wax content, such as corn oil, sunflower oil, olive oil, pennycress oil, certain poultry fats, and possibly algal oils. Because of their solubility in alkyl esters across a wide temperature range, waxes cannot always be fully removed in a cost-effective manner using a combination of a pretreatment (110) and FFA refining (120) process and a cold filtration process or similar winterization technique. Cold filtration techniques may use diatomaceous earth (DE) or other filter media to increase the effectiveness of the filtration.

In another embodiment, the dried biodiesel (158) is subjected to a membrane filtration process in unit (310) such that high melting components, such as proteins, waxes, and certain unsaponifiables, are condensed and removed below their melting point. Membrane filtration may occur at cold temperatures such that condensed particles are more easily filtered or at higher temperatures using membranes with very small pores that can separate larger or more polar molecules from a solution (e.g., nanofiltration). In this way, the dried biodiesel (158) can be made to meet commercial biodiesel specifications. Membrane filtration techniques may include ceramic membranes, polymer membranes, molecular sieves, and carbon fibers or nanotubes. In one embodiment, product leaving the phase separation unit (300) may directly enter a membrane filtration unit which removes both methanol and water rather than passing through a biodiesel alcohol stripper (305).

In another embodiment, the dried biodiesel (158) is subjected to a resin filtration process in unit (310) such that impurities, including water, are removed. In this way, the dried biodiesel (158) can be made to meet commercial biodiesel specifications. Resin filtration techniques may include dry wash resins, ion-exchange resins and other absorbent resins. In one embodiment, product leaving the phase separation unit (275) or (300) may directly enter a resin filtration unit which may remove methanol, glycerin, water and other impurities rather than passing through additional purification units.

In another embodiment, dried biodiesel (158) from the biodiesel alcohol stripper (305) can be subjected to distillation in unit (310) to remove or reduce the levels of waxes, unsaponifiables, soaps, color compounds, sulfur compounds, high-boiling compounds with acid or base functional groups, and mono-, di-, and triglycerides. Such a distillation process can be performed by various process equipment, including distillation vessels, distillation columns, short path distillation, wiped film evaporators, thin film evaporators, falling film evaporators, and other strategies. The resulting biodiesel is purified (160) and should be commercially acceptable in spite of the problematic components that were present in the initial crude feedstock.

In one embodiment, biodiesel purification unit (310) is a short path distillation process (e.g., a wiped film evaporator) used to reduce levels of sulfur compounds, waxes, soaps, phospholipids, color impurities, high molecular weight compounds such as polymerized fatty acid compounds and compounds with acid functional groups, glycerides (mono-, di- and triglycerides), and unsaponifiable material comprising at least one of sterols, sterol derivatives, proteins, and pigments.

In another embodiment, biodiesel purification unit (310) may be a distillation column when, in addition to the impurities discussed in the preceding paragraph, a particularly low level of monoglycerides is critical for commercial acceptance, such as less than about 0.2 wt %.

In one embodiment, biodiesel distillation in unit (310) purifies the crude biodiesel to reduce protein, wax, and unsaponifiables content such that the purified biodiesel product will pass cold soak filterability tests. In one embodiment biodiesel distillation purifies the crude biodiesel to remove compounds causing a second inflection point and elevated Acid Number when titrated according to ASTM D664 Method B. In one embodiment biodiesel distillation purifies the crude biodiesel to remove other acidic compounds such that the purified biodiesel product will have a reduced Acid Number. In one embodiment, the purified biodiesel product (160) has an Acid Number of less than about 1, 0.5, 0.3 or 0.1. In one embodiment biodiesel distillation purifies the crude biodiesel to remove unsaponifiables such that the purified biodiesel product will have increased ester content. In one embodiment biodiesel distillation purifies the crude biodiesel to reduce color compounds such that the purified biodiesel product will have a lighter color than the original feedstock. In one embodiment biodiesel distillation purifies the crude biodiesel to reduce color compounds such that the purified biodiesel product will meet color requirements for customer acceptance and/or will not appear similar to diesel dyed for off-road use. In one embodiment biodiesel distillation purifies the crude biodiesel to remove glycerides such that the purified biodiesel product will meet commercial monoglyceride specifications such as the new monoglyceride specification in ASTM D6751 and future glyceride specifications should they be introduced.

In one embodiment, biodiesel distillation occurs between 200-300° C. and 800-0 Torr. In another embodiment, biodiesel distillation occurs between 230-290° C. and 40-0 Torr. In yet another, biodiesel distillation occurs between 240-280° C. and 5-0.01 Torr.

In one embodiment, the biodiesel product produced from the biodiesel purification process will have a wax content of less than 0.1 wt %, an unsaponifiables content of 2 wt % or less, a soap content of 50 ppm or less, a sulfur content of 500 ppm or less, a monoglyceride content less than 0.6 wt %, a cold soak filtration result of 360 seconds or less and a lighter color than the original feedstock.

In another embodiment, the biodiesel product produced from the biodiesel purification process will have a wax content of less than 0.05 wt %, an unsaponifiables content of 1 wt % or less, a soap content of 20 ppm or less, a sulfur content of 15 ppm or less, a monoglyceride content less than 0.5 wt %, a cold soak filtration result of 240 seconds or less and a lighter color than the original feedstock.

In one embodiment, the biodiesel product produced from the biodiesel purification process will have a wax content of less than 0.01 wt %, an unsaponifiables content of 0.5 wt % or less, a soap content of 10 ppm or less, a sulfur content of 10 ppm or less, a monoglyceride content less than 0.4 wt %, a cold soak filtration result of 200 seconds or less and a lighter color than the original feedstock.

The invention is illustrated in detail below with reference to the examples, but without restricting it to them.

EXAMPLES

Example 1

Feedstock Properties and Corresponding Processing Options

Feedstock properties determine how the feedstock should be processed in order to produce a commercially acceptable biodiesel. However, there are usually multiple processing options available and the chosen pathway is constrained by a combination of what is economically feasible and end-product quality. Depending on the feedstock more than one acceptable feedstock pretreatment (110), free fatty acid refining (120) and biodiesel refining (155) processing pathways may exist. Table 1 outlines a number of feedstock refining pathways that correspond to the Process Units depicted in FIG. 2, though other options may exist.

TABLE 1

Feedstock Refining Pathways
Feedstock Refining -110, 120

| Option | Pretreatment - 110 | FFA Refining - 120 | FIG. 2 Process Units |
| --- | --- | --- | --- |
| A1 | Chemical Refining + Bleaching (A) | Bypass (1) | 205, 230 |
| B1 | Degumming + Bleaching (B) | Bypass (1) | 210, 230 |
| B2 | Degumming + Bleaching (B) | FFA Stripping (2) | 210, 230, 235 |
| B3 | Degumming + Bleaching (B) | FFA Conversion (3) | 210, 230, 250 |
| B4 | Degumming + Bleaching (B) | FFA Stripping + FFA Conversion (4) | 210, 230, 235, 250 |
| C2 | Bleaching (C) | FFA Stripping (2) | 230, 235 |
| C3 | Bleaching (C) | FFA Conversion (3) | 230, 250 |
| C4 | Bleaching (C) | FFA Stripping + FFA Conversion (4) | 230, 235, 250 |

Table 2 outlines biodiesel refining pathways that correspond to biodiesel purification unit (310) in FIG. 2. It should be noted that the filtration option may include any number of filtration techniques, including cold filtration, membrane filtration, the use of chemically-active adsorbents or resins (i.e., "dry washing"), or other such methods. Similarly the distillation option may include any number of distillation techniques, including atmospheric distillation, vacuum distillation, or other such methods.

TABLE 2

Biodiesel Refining Pathways
Biodiesel Refining -155

| Option | Biodiesel Purification -310 |
| --- | --- |
| F | Filtration |
| D | Distillation |

Table 3 provides a list of feedstocks, feedstock properties, and corresponding processing pathways with respect to the feedstock refining and biodiesel refining pathways listed in Table 1 and Table 2, respectively. The processing pathways in Table 3 are examples of how particular feedstocks could be processed to produce commercially acceptable biodiesel, however, other acceptable pathways may exist. Each feedstock requires an appropriate combination of feedstock refining pathway and biodiesel refining pathway in order to produce commercially acceptable biodiesel.

TABLE 3

Example Feedstock Properties and Processing Pathways

| Crude Feedstock Examples | FFA Content | Wax Content | Color | Sulfur | Unsaponifiables | Processing Pathway Options |
|---|---|---|---|---|---|---|
| Corn Oil | High | High | High | Low | High | C2 + D, C3 + D, C4 + D |
| Poultry Fat | High | High | High | High | Low | B2 + D, B3 + D, B4 + D |
| Crude Soybean/Canola Oil | Low | Low | Low | Low | Low | A1 + F, B1 + F |
| Used Cooking Oil | High | Low | High | Low | Low | B2 + D, B3 + D, B4 + D, C2 + D, C3 + D, C4 + D |
| Pennycress/Algae/Other | High/Low | High/Low | High | Low | High/Low | A1 + D, B1 + D, B2 + D, B3 + D, B4 + D |
| Fatty Acid Distillate | High | Low | High | High | Low | C3 + F, C3 + D |

Example 2

Acid Esterified Corn Oil Biodiesel with and without Distillation Purification Corn oil from a grain ethanol process was converted into commercially acceptable biodiesel using an acid esterification FFA refining process coupled with cold filtration and distillation biodiesel refining steps. Two samples of corn oil biodiesel were obtained: one immediately after cold filtration using diatomaceous earth (DE) and a second after both cold filtration and distillation to compare the effects. The crude corn oil feedstock was acid esterified with methanol using homogeneous sulfuric acid ($H_2SO_4$) catalyst to convert free fatty acids to methyl esters. The strong acid used during esterification was neutralized with sodium hydroxide (NaOH) before a water wash. Once the feedstock was dried it was sent to a base-catalyzed transesterification process. After being separated from the glycerin and removing the methanol and water, the dried biodiesel was subjected to purification by cold filtration or distillation in a wiped-film evaporator. The physical and chemical properties of the dried biodiesel before and after distillation are provided in Table 4 below. Cold filtration of the dried biodiesel using DE produces biodiesel with acceptable Cold Soak Filtration Time, Acid Number, Sulfur, and Monoglycerides according to ASTM D6751. However, distillation of the cold filtered, dried biodiesel clearly reduces the wax content (as indicated by Turbidity), Acid Number (and number of inflection points), and Gardner Color (a yellow-to-red color scale) which are particularly problematic properties for corn oil biodiesel. Therefore, a combination of esterification of free fatty acids (FFA) and biodiesel distillation can be used to produce purified corn oil biodiesel that meets more stringent commercial biodiesel specifications than a combination of FFA esterification and cold filtration.

TABLE 4

Properties of Acid Esterified Corn Oil Biodiesel with Cold Filtration and Distillation

| | Esterified Corn Oil Biodiesel | |
|---|---|---|
| Properties | Cold Filtered | Cold Filtered & Distilled |
| Wax Reduction (Indirect Methods): | | |
| Cold Soak Filtration Time | 96 | — |
| [ASTM D7501] (s) | | |
| Turbidity (Nephelometric Turbidity Unit or NTU) | 22.3 | 1.4 |
| Acid Number per ASTM D664 Method B (mg KOH/g) | 0.453 | 0.298 |
| Number of Inflection points | 2 | 1 |
| Nitrogen (ppm) | 14.5 | 4.8 |
| Sulfur (ppm) | 6.0 | 3.0 |
| Monoglycerides (wt %) | 0.49 | 0.53 |
| Diglycerides (wt %) | 0.06 | <0.005 |
| Triglycerides (wt %) | <0.005 | <0.005 |
| Color: | | |
| Gardner Color (ASTM D1544) | 15 | 9 |
| Resemblance to Dyed Diesel | yes | no |

Example 3

FFA Stripped Corn Oil Biodiesel with and without Distillation Purification Compared to Filtration Corn oil from a grain ethanol process was converted into biodiesel using an FFA stripping process for FFA refining followed by transesterification of the stripped feedstock and two purification techniques: room temperature filtration using a single-layer paper filter and distillation. A sample of dried corn oil biodiesel was obtained before and after the biodiesel refining units to compare the effectiveness of each method in conjunction with the FFA refining approach. The crude corn oil feedstock was stripped of FFA before entering a base-catalyzed transesterification process. After being separated from the glycerin and removing the methanol and water, the dried biodiesel was subjected to purification by either a filtration step or distillation in a wiped-film evaporator. The physical and chemical properties of the biodiesel before and after purification by filtration or distillation are provided in Table 5 below. The filtration and distillation processes both improve the biodiesel quality compared to unpurified dried biodiesel. However, the effect of distillation is more pronounced than filtration especially in terms of relative wax reduction (as indicated by the Cold Soak Filtration time and Turbidity), Acid Number, unsaponifiables, nitrogen, sulfur, di- and triglycerides, and color.

Although distillation was able to reduce the number of inflection points and overall Acid Number, the high initial Acid Number of the unpurified dried corn oil biodiesel used in this trial indicates the importance of having both FFA refining and biodiesel refining. In this laboratory example, the FFA refining process was not optimized and was therefore not able to sufficiently remove sufficient FFAs to produce biodiesel that meet the ASTM D6751 specification for Acid Number.

TABLE 5

Properties of Stripped Corn Oil Biodiesel with Filtration or Distillation

| Properties | Stripped Corn Oil Biodiesel | | |
|---|---|---|---|
| | Unpurified | Filtered | Distilled |
| Wax Reduction (Indirect Methods): | | | |
| Cold Soak Filtration Time [ASTM D7501] (s) | 720$^a$ | 720$^b$ | 176 |
| Turbidity (Nephelometric Turbidity Unit or NTU) | 84.0 | 29.0 | 1.3 |
| Acid Number per ASTM D664 Method B (mg KOH/g) | 1.021 | 0.955 | 0.908 |
| Number of Inflection points | 2 | 2 | 1 |
| Unsaponifiables (wt %) | 0.77% | 0.97% | 0.27% |
| Nitrogen (ppm) | 23.1 | 21.5 | 6.7 |
| Sulfur (ppm) | 6.7 | 6.5 | 3.7 |
| Monoglycerides (wt %) | 0.62 | 0.61 | 0.64 |
| Diglycerides (wt %) | 0.09 | 0.10 | <0.005 |
| Triglycerides (wt %) | 0.04 | 0.04 | <0.005 |
| Color: | | | |
| Gardner Color (ASTM D1544) | 11 | 11 | 5 |
| Resemblance to Dyed Diesel | yes | yes | no |

$^a$150 mL out of 300 mL remaining after 720 s
$^b$120 mL out of 300 mL remaining after 720 s Example 4

FFA Stripped Used Cooking Oil Biodiesel with and without Distillation Purification Compared to Cold Filtration A mixture of used cooking oil (UCO) and poultry fat was converted into commercially acceptable biodiesel using an FFA stripping FFA refining process followed by transesterification and two biodiesel refining techniques: cold filtration using DE and distillation. A sample of biodiesel was obtained before cold filtration and distillation to compare the effectiveness of each method. The biodiesel feedstock mixture was stripped of FFA before entering a base-catalyzed transesterification process. After being separated from the glycerin and removing the methanol and water, the dried biodiesel was subjected to purification by either a cold-filtration step using DE or distillation in a wiped-film evaporator. The physical and chemical properties of the biodiesel before and after purification by cold-filtration or distillation are provided in Table 6 below. The filtration and distillation processes both improve the biodiesel quality compared to unpurified dried biodiesel, particularly with respect to cold soak filterability and sulfur. However, the effect of distillation is more pronounced than cold filtration especially in terms of removing color compounds and lowering Acid Number, Cold Soak Filtration time, nitrogen and sulfur.

TABLE 6

Properties of Stripped Used Cooking Oil & Poultry Fat Biodiesel with Cold Filtration or Distillation

| Properties | Stripped UCO/Poultry Fat Biodiesel | | |
|---|---|---|---|
| | Unpurified | Cold Filtered | Distilled |
| Wax Reduction (Indirect Methods): | | | |
| Cold Soak Filtration Time [ASTM D7501] (s) | 720$^a$ | 100 | 78 |
| Turbidity (Nephelometric Turbidity Unit or NTU) | 5.6 | 3.2 | 0.5 |
| Acid Number per ASTM D664 Method B (mg KOH/g) | 0.353 | 0.346 | 0.287 |
| Number of Inflection points | 1 | 1 | 1 |
| Unsaponifiables (wt %) | 0.45% | 0.36% | 0.36% |
| Nitrogen (ppm) | 51.3 | 54.4 | 24.4 |
| Sulfur (ppm) | 12.4 | 9.4 | 8.4 |
| Monoglycerides (wt %) | 0.29 | 0.30 | 0.30 |
| Diglycerides (wt %) | 0.09 | 0.08 | <0.005 |
| Triglycerides (wt %) | <0.005 | 0.00 | <0.005 |
| Color: | | | |
| Petroleum Products (ASTM D1500) | 4 | 4 | 0.5 |
| Resemblance to Dyed Diesel | no | no | no |

$^a$125 mL out of 300 mL remaining after 720 s

As a result of the high degree of variability in the identity and quantity of impurities found in feedstocks for biodiesel, particularly low-cost crude feedstocks, a number of process steps as disclosed in the embodiments of the invention may be employed as disclosed herein to convert highly impure feedstock into high quality and fully acceptable biodiesel. These various embodiments are described in sufficient detail to enable one of ordinary skill in the art to practice the invention, and it is to be understood that modifications to the various disclosed embodiments may be made by a skilled artisan.

Where methods and steps described above indicate certain events occurring in certain order, those of ordinary skill in the art will recognize that the ordering of certain steps may be modified and that such modifications are in accordance with the principles of the invention. Additionally, certain steps may be performed concurrently in a parallel process when possible, as well as performed sequentially.

All publications, patents, and patent applications cited in this specification are herein incorporated by reference in their entirety as if each publication, patent, or patent application were specifically and individually put forth herein.

The embodiments, variations, and figures described above provide an indication of the utility and versatility of the present invention. Other embodiments that do not provide all of the features and advantages set forth herein may also be utilized, without departing from the spirit and scope of the present invention. Such modifications and variations are considered to be within the scope of the principles of the invention defined by the claims.

What is claimed is:
1. A method for producing a purified biodiesel from a first feedstock comprising:
   a. removing free fatty acids from said first feedstock in a free fatty acid stripping process to produce a refined feedstock and a fatty acid distillate;
   b. transesterifying said refined feedstock to produce a first crude biodiesel;

c. distilling said first crude biodiesel to produce the purified biodiesel and a distillation bottoms; and
d. converting the fatty acid distillate to a second feedstock using a glycerolysis process.

2. The method of claim 1, further comprising the step of using a transesterification process to convert said second feedstock to a second crude biodiesel.

3. The method of claim 2, further comprising the step of combining the second crude biodiesel with the first crude biodiesel and distilling the first crude biodiesel and second crude biodiesel together in step (c).

4. The method of claim 1, further comprising the step of combining the second feedstock with the refined feedstock and transesterifying the refined feedstock and second feedstock together in step (b).

5. The method of claim 1 further comprising the step of pretreating said first feedstock to produce a pretreated feedstock before the free fatty acids are removed from said first feedstock and using the pretreated feedstock as the first feedstock in step (a).

6. The method of claim 1, wherein said first feedstock contains between about 0.2 wt % and about 30 wt % free fatty acids.

7. The method of claim 1, wherein said first feedstock comprises at least one of corn oil, palm oils, fatty acid distillates, distillation bottoms, brown grease, poultry fat, used cooking oil, pennycress oil, algae oil, soybean oil, and canola oil.

8. The method of claim 1, wherein said purified biodiesel exhibits a single inflection point when analyzed for Acid Number with ASTM D664 Method B.

9. The method of claim 1, wherein said purified biodiesel has a lower Acid Number than the first crude biodiesel.

10. The method of claim 1, wherein said purified biodiesel has a lighter color than the first crude biodiesel.

11. The method of claim 1, wherein said purified biodiesel has a lower wax content than the first crude biodiesel.

12. The method of claim 1, wherein said first purified biodiesel has a lower sulfur content than the first crude biodiesel.

13. The method of claim 1, wherein said purified biodiesel has a lower unsaponifiable impurities content than the first crude biodiesel.

14. The method of claim 1, wherein said purified biodiesel has a wax content of less than 0.1 wt %, an unsaponifiables content of 2 wt % or less, a soap content of 50 ppm or less, a sulfur content of 500 ppm or less, a monoglyceride content less than 0.6 wt %, a cold soak filtration test result of 360 seconds or less and a lighter color than the first feedstock.

15. The method of claim 1, further comprising the step of utilizing the distillation bottoms as a renewable fuel feedstock.

16. The method of claim 1, further comprising the step of utilizing the distillation bottoms as a fuel.

17. A method for producing purified biodiesel from a first feedstock comprising:

a. removing free fatty acids from said first feedstock to produce a refined feedstock and a fatty acid distillate;
b. transesterifying said refined feedstock to produce a first crude biodiesel;
c. refining said first crude biodiesel to produce a first purified biodiesel; and
d. converting the fatty acid distillate to a second feedstock using a glycerolysis process.

18. The method of claim 17, wherein said second feedstock is further processed to produce a second crude biodiesel.

19. The method of claim 18 wherein said second crude biodiesel is processed with at least one of the refined feedstock and the first crude biodiesel to produce the first purified biodiesel.

20. The method of claim 17, wherein said first crude biodiesel is refined via at least one of a distillation process and a filtration process to produce the first purified biodiesel.

21. The method of claim 17 wherein a distillation bottoms are separated from the crude biodiesel during the refining step.

22. The method of claim 21, further comprising the step of utilizing the distillation bottoms as a renewable fuel feedstock.

23. The method of claim 21 further comprising the step of utilizing the distillation bottoms as a fuel.

24. A method for producing a purified biodiesel from a feedstock containing corn oil comprising:

a. refining the feedstock containing corn oil in a free fatty acid stripping process to produce a refined feedstock and a fatty acid distillate;
b. transesterifying said refined feedstock to produce a crude biodiesel;
c. distilling said crude biodiesel to produce said purified biodiesel and a distillation bottoms; and
d. utilizing the fatty acid distillate as a renewable fuel feedstock.

25. The method of claim 24, wherein the purified biodiesel has a lighter color than the feedstock containing corn oil.

26. The method of claim 24, wherein the purified biodiesel has a wax content of less than 0.1 wt %, an unsaponifiables content of 2 wt % or less, a soap content of 50 ppm or less, a sulfur content of 500 ppm or less, a monoglyceride content less than 0.6 wt %, a cold soak filtration result of 360 seconds or less and a lighter color than the feedstock containing corn oil.

27. The method of claim 24, further comprising the step of utilizing the distillation bottoms as a renewable fuel feedstock.

28. The method of claim 24 further comprising the step of utilizing the distillation bottoms as a fuel.

29. A product produced by the process of claim 24.

30. The method of claim 17 wherein said second feedstock is processed with the refined feedstock to produce the first crude biodiesel.

* * * * *